(12) United States Patent
Palmer et al.

(10) Patent No.: US 8,586,912 B1
(45) Date of Patent: Nov. 19, 2013

(54) LOW-NOISE OPTICAL CURRENT SOURCE

(75) Inventors: Timothy John Palmer, Ely (GB); Paul Nicholas Winter, Lakenheath (GB)

(73) Assignee: Covidien LP, Mansfield, MA (US)

( * ) Notice: Subject to any disclaimer, the term of this patent is extended or adjusted under 35 U.S.C. 154(b) by 202 days.

(21) Appl. No.: 13/283,041

(22) Filed: Oct. 27, 2011

(51) Int. Cl.
*G01D 18/00* (2006.01)
*A61B 5/00* (2006.01)

(52) U.S. Cl.
USPC ........................................ 250/252.1; 600/331

(58) Field of Classification Search
USPC ............ 250/252.1, 578.1; 600/322–340, 310; 356/39–41
See application file for complete search history.

(56) References Cited

U.S. PATENT DOCUMENTS

| | | | |
|---|---|---|---|
| 5,348,005 A * | 9/1994 | Merrick et al. | 600/330 |
| 5,783,821 A | 7/1998 | Costello, Jr. | |
| 5,807,247 A | 9/1998 | Merchant et al. | |
| 5,891,025 A | 4/1999 | Buschmann et al. | |
| RE39,268 E | 9/2006 | Merrick et al. | |
| 7,428,432 B2 | 9/2008 | Ali et al. | |
| 2006/0247507 A1* | 11/2006 | Ruiter | 600/331 |
| 2008/0030468 A1 | 2/2008 | Ali et al. | |
| 2008/0177160 A1 | 7/2008 | Ali et al. | |

* cited by examiner

*Primary Examiner* — Thanh Luu
*Assistant Examiner* — Renee Naphas
(74) *Attorney, Agent, or Firm* — Shvarts & Leiz LLP

(57) ABSTRACT

Systems, methods for manufacturing, and devices for producing an output current that simulates a current generated by an optical patient sensor are provided. An optical patient sensor includes a sensor light source having a first characteristic profile and a sensor photodetector having a second characteristic profile. The current source includes a light source having a characteristic profile similar to the first characteristic profile and indicative of interchangeability between the light source and the sensor light source, and a first photodetector configured to produce an output current in response to receiving light from the light source, the first photodetector having a characteristic profile similar to the second characteristic profile and indicative of interchangeability between the sensor photodetector and the first photodetector.

22 Claims, 9 Drawing Sheets

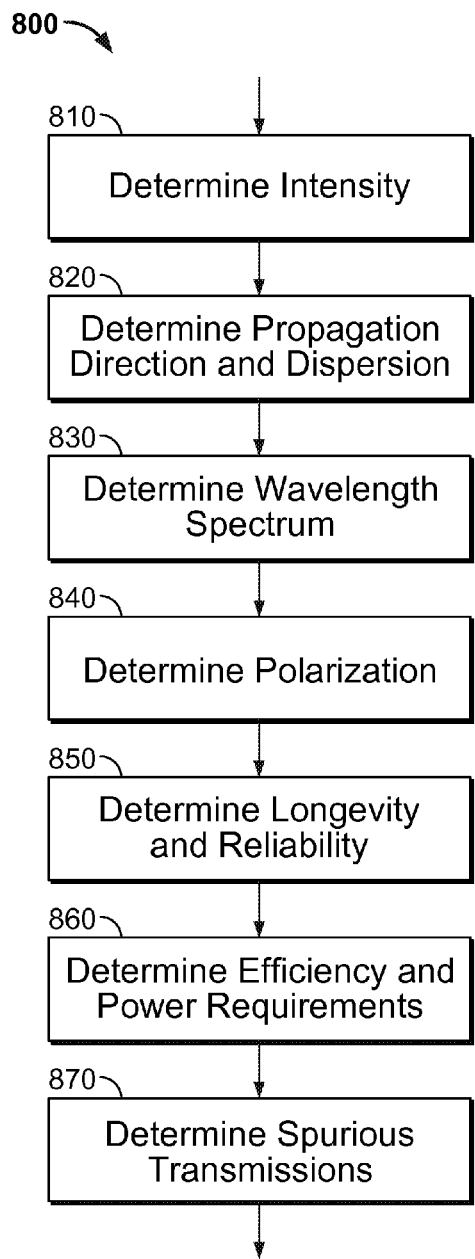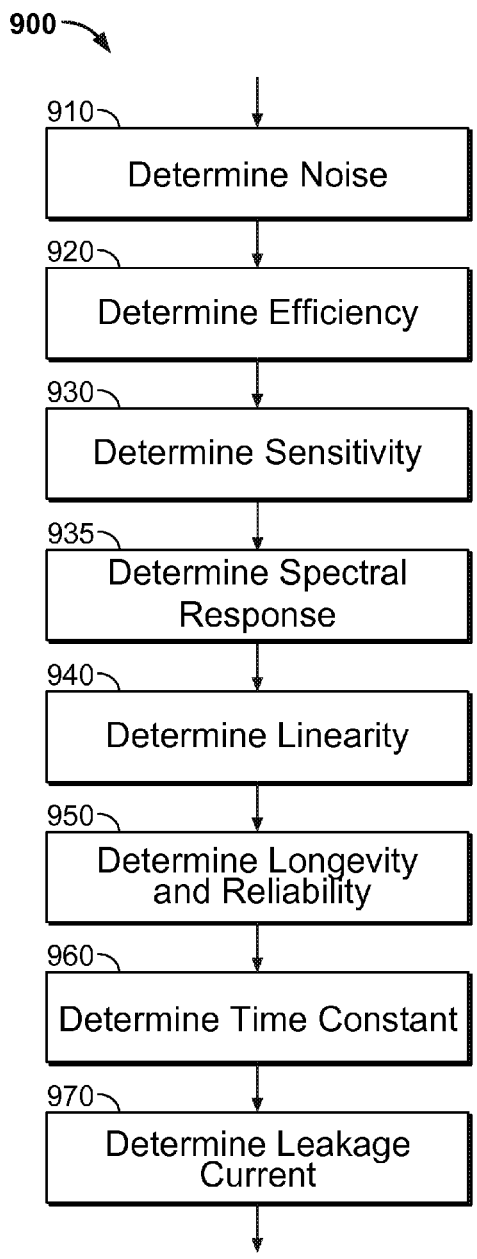
FIG. 8
FIG. 9

LOW-NOISE OPTICAL CURRENT SOURCE

SUMMARY

Described herein are systems, devices, and methods for providing and manufacturing a current source that produces an output current that simulates a current generated by an optical patient sensor. An optical patient sensor may include a sensor light source having a first characteristic profile and a sensor photodetector having a second characteristic profile. The current source may include a light source configured to emit light in response to a drive signal, the light source having a characteristic profile similar to the first characteristic profile as to indicate interchangeability between the light source and the sensor light source. The current source may also include a first photodetector configured to produce the output current in response to receiving light from the light source, the first photodetector having a characteristic profile similar to the second characteristic profile as to indicate interchangeability between the sensor photodetector and the first photodetector. The current source may also include a control unit configured to receive a signal indicative of light emitted by the light source and provide the drive signal to the light source based at least in part on the received signal indicative of light emitted by the light source and a waveform control signal.

In some implementations, the first characteristic profile and the characteristic profile of the light source include at least one of a common manufacturing specification and a common manufacturing batch. For example, a common manufacturing specification may include at least one of an intensity, a propagation direction, a dispersion, a wavelength spectrum, a polarization, and a noise level. In some implementations, the second characteristic profile and the characteristic profile of the first photodetector include at least one of a common manufacturing specification and a common manufacturing batch. For example, a common manufacturing specification may include at least one of a noise level, a sensitivity, a spectral response, and a linearity. In some implementations, the characteristic profile of the light source includes a characteristic with a value within a tolerance range of a value of a corresponding characteristic included in the first characteristic profile. The characteristic profile of the first photodetector may include a characteristic with a value within a tolerance range of a value of a corresponding characteristic included in the second characteristic profile.

In some implementations, the current source includes a connector configured to couple the output current to a patient monitoring device. The current source may include processing equipment configured to generate the waveform control signal based on at least one of a waveform stored in a memory and a user selection of one or more waveform features. The processing equipment may be included in a control module, and the current source may further include a connector configured to removably couple the current source to the control module.

Also described herein are methods of manufacturing a current source for producing an output current that simulates a current generated by an optical patient sensor. A light source is selected having a characteristic profile similar to the first characteristic profile as to indicate interchangeability between the light source and the sensor light source, and a photodetector is selected having a characteristic profile similar to the second characteristic profile as to indicate interchangeability between the photodetector and the sensor photodetector. In some implementations, characteristics of the light source or the photodetector or both are tested. The photodetector is configured to produce the output current in response to receiving light from the light source. The light source and photodetector are coupled to a control unit, and the control unit is configured to provide a drive signal to the light source. A connector is coupled to the photodetector, whereby the output current is provided to the connector.

In some implementations, the current source is installed within a test unit for a pulse oximetry monitor, and the connector is configured to couple with a pulse oximetry monitor connector to provide the output current to the pulse oximetry monitor. The connector may be configured to couple with an optical patient sensor connector included with the pulse oximetry monitor. In some implementations, the control unit is coupled to a connector configured to removably couple the current source to a separate control module, the control module configured to provide a waveform control signal to the control unit and the control unit configured to provide a drive signal based at least in part on the waveform control signal. In some implementations, a second current source is provided for producing an output current that simulates a current generated by a second, different optical patient sensor, wherein the second current source is configured to couple to the control module after the current source is removed. In some implementations, a light deflecting device is installed to deflect at least some of the light emitted by the light source away from the photodetector.

BRIEF DESCRIPTION OF THE DRAWINGS

The above and other features of the present invention, its nature and various advantages will be more apparent upon consideration of the following detailed description, taken in conjunction with the accompanying drawings in which:

FIG. 8 is a flow chart of illustrative steps of a process used to determine characteristics of a candidate light source for inclusion in an optical front-end;

FIG. 9 is a flow chart of illustrative steps of a process used to determine characteristics of a candidate detector for inclusion in an optical front-end.

DETAILED DESCRIPTION

Figure 1:
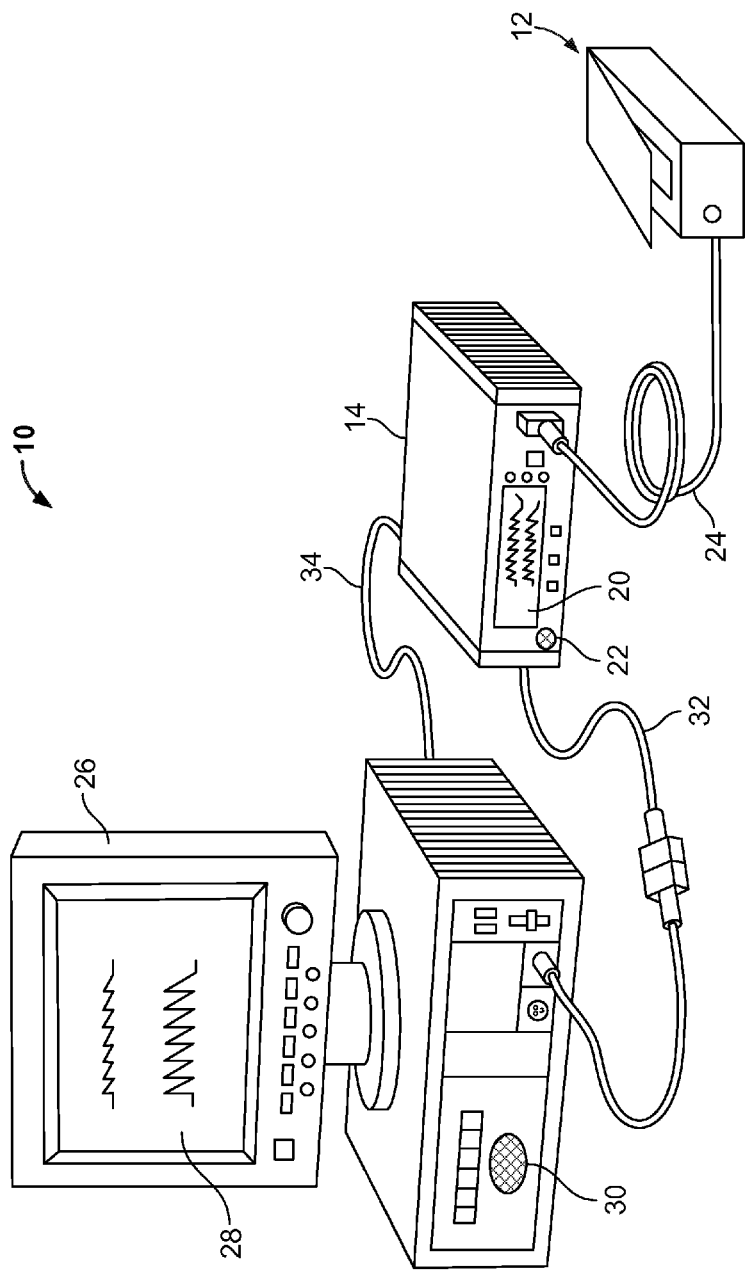
FIG. 1 is a perspective view of a pulse oximetry system arranged in a test mode in accordance with an embodiment.

An oximeter is a medical device used to determine the oxygen saturation of the blood. One common type of oximeter is a pulse oximeter, which measures oxygen saturation of a patient's blood and changes in blood volume in the skin. A pulse oximeter may also be used to measure a pulse rate of the patient. Pulse oximeters typically make measurements using one or more sensors (for example, optical sensors) and may display various blood flow characteristics of the patient. For example, a pulse oximeter may display a oxygen saturation of hemoglobin in a patient's arterial blood on a monitor.

During normal operation (also referred to as "non-test" operation), an oximeter may be attached to a sensor that is placed on a patient, typically on a fingertip, toe, forehead or earlobe, or in the case of a neonate, across a foot. The sensor passes light into the tissue using a light source and photoelectrically senses the absorption of light in the tissue. Red and infrared wavelengths may be emitted by the sensor. It has been observed that highly oxygenated blood will absorb relatively less red light and more infrared light than blood with a lower oxygen saturation. By comparing the intensities of two wavelengths at different points in the cardiac pulse cycle, a pulse oximeter estimates the blood oxygen saturation of hemoglobin in arterial blood.

The sensor connected to the oximeter includes a detector that, in normal operation, measures the intensity of light that is received by the detector as a function of time. A signal representing light intensity versus time or a mathematical manipulation of this signal (for example, a scaled version thereof, a log taken thereof, a scaled version of a log taken thereof, or other manipulation) may be referred to as a photoplethysmograph (PPG) signal. The term "PPG signal," as used herein, may also refer to an absorption signal (that is, representing the amount of light absorbed by the tissue) or any suitable mathematical manipulation thereof. The PPG signal may then be used by the oximeter to calculate and display one or more blood flow characteristics of a patient.

It may be advantageous to test a pulse oximeter (in a "test mode" or "test operation") to ensure that the pulse oximeter is functioning properly. However, test signals produced by common test units may not simulate actual signals derived from a sensor during a normal operation of the pulse oximeter. The systems and methods disclosed herein provide test signals that simulate the output of an actual sensor during normal operation of the pulse oximeter. In certain implementations, a test unit is provided that adapts to changing conditions of the pulse oximeter's internal components, for example, due to temperature changes and/or a gradual changes due to aging of electrical and/or optical components of the test unit. A test unit may simulate a plurality of sensor types, corresponding to different sensors that may be used with the pulse oximeter in a real deployment (for example, in a medical facility). For example, a pulse oximeter may be compatible with sensors designed for each of neonates, children, and adults, and the test unit may be configured to simulate a typical current output signal produced by each of these different sensor types.

FIG. 1 is a perspective view of a pulse oximetry system 10 arranged in a test mode. The pulse oximetry system 10 includes test unit 12 and pulse oximetry monitor 14. The test unit 12 may be used to determine whether the pulse oximetry system 10 is functioning properly. The test unit 12 includes a controller that simulates a signal derived from a patient, for example, a PPG signal. The test unit 12 is connected to the pulse oximetry monitor 14 using a cable 24. The test unit 12 may draw its power from the pulse oximetry monitor 14. Alternatively, the test unit 12 may be wirelessly connected to the pulse oximetry monitor 14 and the test unit 12 may include its own battery or similar power supply (not shown). Monitor 14 may be configured to calculate simulated physiological parameters of a simulated patient based at least in part on the signals received from the test unit 12. Monitor 14 includes a display 20 configured to display the simulated physiological parameters. In the embodiment shown, the pulse oximetry monitor 14 includes a speaker 22 to provide an audible sound that may be used in various other embodiments, such as for example, sounding an audible alarm in the event that simulated physiological parameters are not within a predefined normal range.

In the illustrated embodiment, the pulse oximetry system 10 also includes a multi-parameter patient monitor 26. The monitor may incorporate a cathode ray tube type, a flat panel display (as shown) such as a liquid crystal display (LCD) or a plasma display, or any other type of display now known or later developed. The multi-parameter patient monitor 26 is configured to calculate physiological parameters and to provide a display 28 for information from the pulse oximetry monitor 14 and from other medical monitoring devices or systems (not shown). For example, the multiparameter patient monitor 26 may be configured to display an estimate of a patient's blood oxygen saturation generated by the pulse oximetry monitor 14 (referred to as an "SpO$_2$" measurement), pulse rate information from the pulse oximetry monitor 14 and blood pressure from a blood pressure monitor (not shown) on the display 28. The multi-parameter patient monitor 26 may include a speaker 30 to provide audible alarms or other alerts.

Monitor 14 is communicatively coupled to the multi-parameter patient monitor 26 via a cable 32 or a cable 34 that is coupled to a sensor input port or a digital communications port, respectively and/or may communicate wirelessly (not shown). In addition, the pulse oximetry monitor 14 and/or the multi-parameter patient monitor 26 may be coupled to a network to enable the sharing of information with servers or other workstations (not shown). Monitor 14 may be powered by a battery (not shown) or by a conventional power source such as a wall outlet.

The test unit 12 includes a current source that simulates a signal produced by an actual patient sensor used by the pulse oximetry system 10. Specifically, the output current of the test unit 12 is designed to be identical to, or nearly identical to, an output current of an actual patient sensor used by the pulse oximetry system 10. For example, in certain implementations, the test unit 12 produces a stable direct current of less than about 100 pA with an alternating current noise component of about 10 pA (root mean square value) or less. In certain implementations, the current produced by the test unit 12 is of a lower output level, and has a lower noise component, than the current produced by typical off-the-shelf (OFS) opto-couplers.

Figure 2:
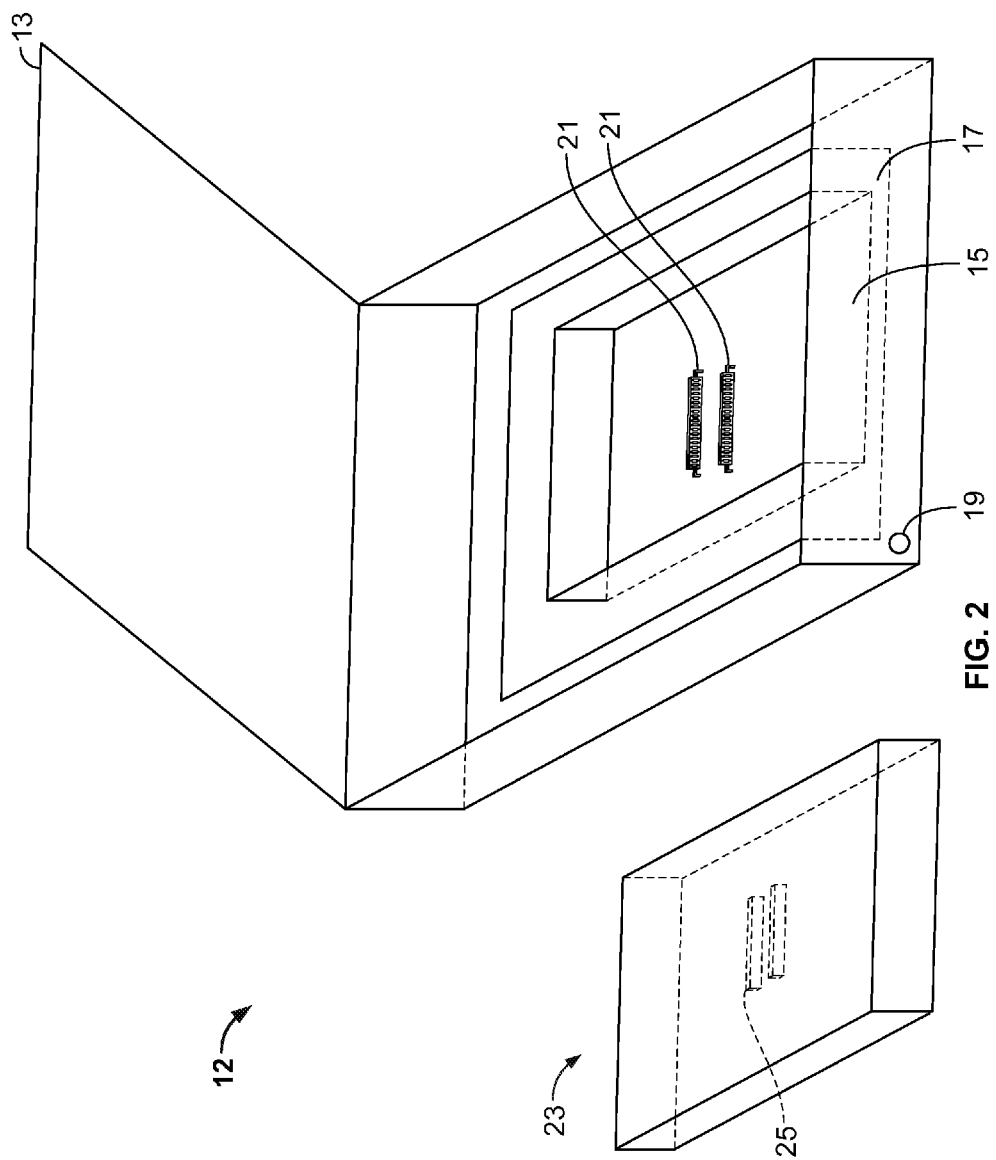
FIG. 2 is a perspective view of a test unit and an optical front-end.

FIG. 2 is a perspective view of the test unit 12 (FIGS. 1 and 2) and the optical front-end 23. The optical front-end 23 includes a light source and one or more photodetectors to simulate a sensor type from among a plurality of sensor types used with the pulse oximetry system 10 (FIG. 1). For example, the pulse oximetry system 10 (FIG. 1) may be capable of working with child and adult sensors, sensors intended for placement on a forehead or digit of a patient, and other sensor types. In certain implementations, the optical front-end 23 includes a light source and one or more photodetectors that correspond to a light emitter and a photodetector of a corresponding patient sensor. In certain implementations, selection of a light emitter for inclusion in the optical front-end 23 is based on criteria including an intensity, polarization, noise, and wavelength spectrum of the light emitter as compared to a light emitter included in the corresponding optical patient sensor. In certain implementations, selection of a photodetector for inclusion in the optical front-end 23 is based on criteria including a linearity, sensitivity, noise, spectral response, and time constant associated with the photodetector compared to a photodetector included in the corresponding optical patient sensor. By inserting an optical front-end corresponding to a particular sensor type into the test unit 12 (FIGS. 1 and 2), the test unit 12 (FIGS. 1 and 2) produces an output current characteristic of the sensor type.

In certain implementations, the optical front-end 23 is enclosed in a stand-alone housing. In certain implementations, the optical front-end 23 is inserted into the test unit 12 (FIGS. 1 and 2) by first opening and/or removing a cover 13 to access a optical front-end port 15, and then interconnecting the optical front-end 23 to the test unit 12 (FIGS. 1 and 2) by fastening a printed circuit board interface connector 25 of optical front-end 23 onto a printed circuit board interface connector 21 of the test unit 12 (FIGS. 1 and 2). One or more connectors included with the optical front-end 23 may disengeably mate with connectors included in the test unit 12, and thus may be readily interchangeable with other optical front-ends in order to simulate a variety of different types of sensors. For example, when a patient sensor is upgraded or changed to include different components, a first optical front-end may be removed and replaced with a second optical front-end including components similar to those included in the new sensor.

The test unit 12 (FIGS. 1 and 2) includes a control module 17. The control module 17 may be located beneath and around the optical front-end port 15, as shown in FIG. 2, or it may be located with a different location and/or orientation relative to the optical front-end port 15. The control module 17 includes circuitry for monitoring operating conditions within the test unit 12 (FIGS. 1 and 2) (including within the optical front-end 23) during operation of the test unit 12 (FIGS. 1 and 2). The control module 17 provides control and feedback functions related to electrical and optical signals to the optical front-end 23. The control module 17 also provides data interconnects between the optical front-end 23 and the pulse oximetry system 10 (FIG. 1) during operation. The test unit 12 (FIGS. 1 and 2) also includes a calibration button 19, that is activated (for example, depressed by a user) to initiate a manual calibration of the optical front-end 23, for example, by calibrating the input to a light source contained within the optical front-end 23. The calibration button 19 adjusts or updates the parameters of the test unit 12 (FIGS. 1 and 2) so that the test unit 12 (FIGS. 1 and 2) better simulates a desired sensor type. In other embodiments, the test unit does not include a calibration button.

Figure 3:
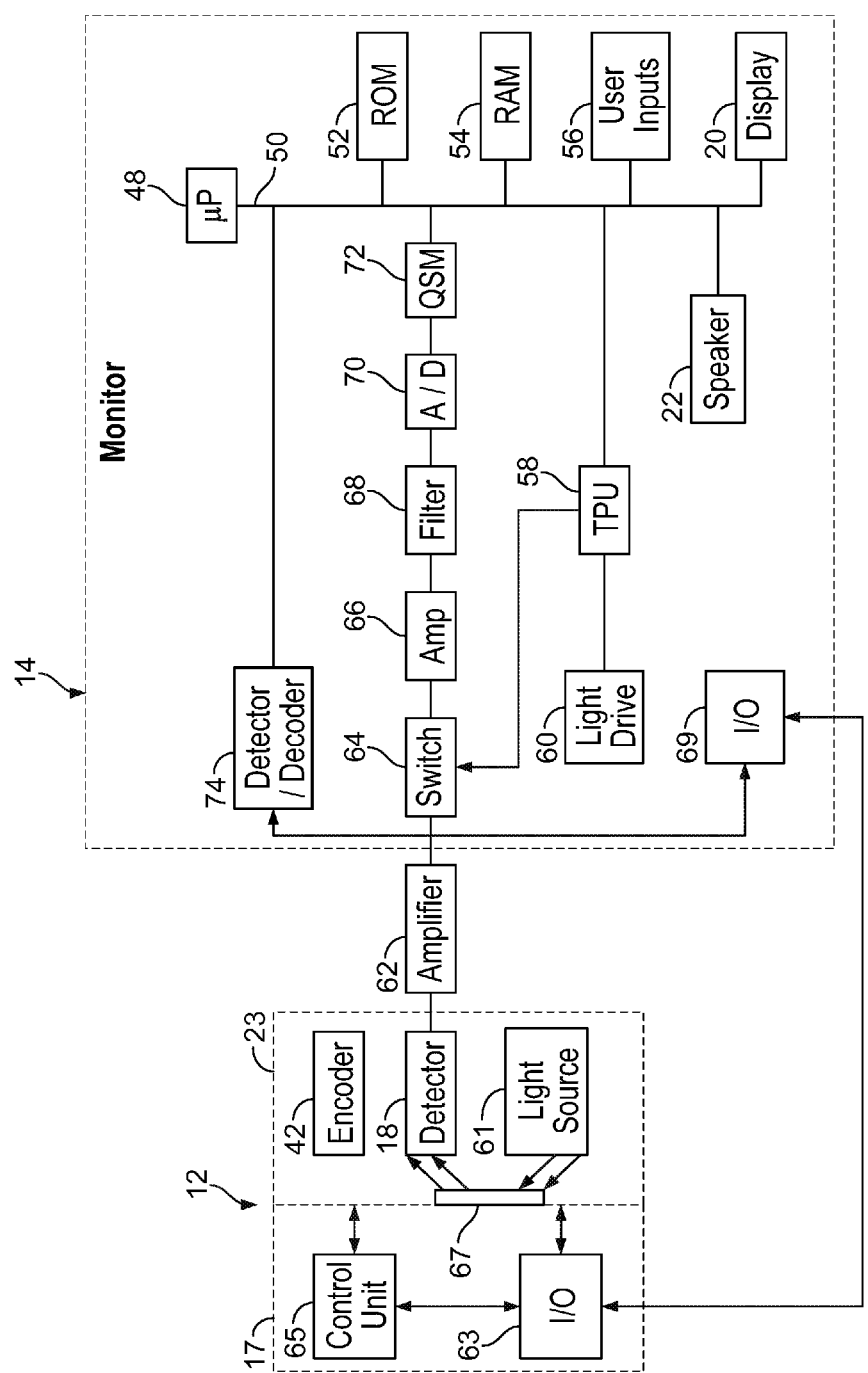
FIG. 3 is an illustrative block diagram of a system containing an optical front-end connected to a test unit and a pulse oximetry monitor.

FIG. 3 is an illustrative block diagram of a system containing the optical front-end 23 (FIGS. 2 and 3) connected to the test unit 12 (FIGS. 1-3) and the pulse oximetry monitor 14 (FIGS. 1 and 3). Optical front-end 23 (FIGS. 2 and 3) includes the light source 61, which may have similar or identical properties to a light source used in a patient sensor during normal operation of the pulse oximetry system 10 (FIG. 1). In certain implementations, the light source 61 includes a RED light emitting light source, such as a RED light emitting diode (LED), and an IR light emitting light source, such as IR LED, for emitting light at desired wavelengths. In certain implementations, the RED wavelength is between about 600 nm and about 700 nm, and the IR wavelength is between about 800 nm and about 1000 nm. It will be understood that, as used herein, the term "light" refers to energy produced by radiative sources derived from one or more of radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. In an alternative implementations, the light source 61 may include a laser-based emitting device.

Optical front-end 23 (FIGS. 2 and 3) includes a detector 18, which has similar or identical properties to a detector normally used in a patient sensor during non-test operation of the pulse oximetry system 10 (FIG. 1). For example, in certain implementations, the detector 18 has linearity, sensitivity, spectral response, and time constant properties that are similar or identical to those of a detector used in the corresponding patient sensor. The detector 18 may be chosen to be responsive to particular energy spectrum emitted by the light source 61. In certain implementations, the detector 18 is configured to detect the intensity of light at RED and IR wavelengths. In certain implementations, light enters the detector 18 after being reflected from a optical device 67, and the detector 18 converts the received light into an electrical signal such as a current signal. The detector 18 thus acts as a current source, via the photovoltaic effect, having an output current approximately (or exactly) proportional to an intensity of the light from the light source 61 that is incident on an exposed portion of the detector 18. The detector 18 sends a current to the pulse oximetry monitor 14 (FIGS. 1 and 3) via an amplifier 62. In alternative implementations, a signal encoder 42 may transfer a current signal to the pulse oximetry monitor 14 (FIGS. 1 and 3) via an input-output interface 63 (and the current signal may be amplified prior to transmission using the input-output interface 63). The input-output interface 63 may be communicably coupled to the pulse oximetry monitor 14 (FIGS. 1 and 3) and to optical front-end 23 (FIGS. 2 and 3), as shown. Although not shown in FIG. 3, the optical front-end 23 (FIGS. 2 and 3) may include one or more detectors in addition to the detector 18. The additional detector or detectors may be used to, for example, generate a secondary current signal that may be used as a feedback signal to perform adjustments to the electrical and optical adjustments to the components of the optical front-end 23 (FIGS. 2 and 3) during operation in the test mode. For example, a control unit 65 may obtain a feedback current signal from a second detector (not shown) of the optical front-end 23 (FIGS. 2 and 3) and use the feedback current signal to control the operation of one or more actuators so as to change the electrical and/or optical properties of the optical front-end 23 (FIGS. 2 and 3). As shown in FIG. 3, input-output interface 63 and control unit 65 are housed in control module 17 (FIGS. 2 and 3).

A current signal received at the pulse oximetry monitor 14 (FIGS. 1 and 3) derived from the detector 18 is used to calculate simulated physiological parameters, such as a simulated patient oxygen saturation, in order to test the pulse oximetry system 10 (FIG. 1) for proper operation. Some or all of the signals received at the pulse oximetry monitor 14 (FIGS. 1 and 3) via an input-output interface 69 are routed to a decoder 74. The decoder 74 translates the received signals to enable a microprocessor 48 to determine thresholds based on algorithms or look-up tables stored in a ROM 52. User inputs 56 may be used to enter information about the simulated patient, such as age, weight, height, diagnosis, medications, treatments, and so forth. In certain embodiments, the display 20 (FIGS. 1 and 3) exhibits a list of values which may generally apply to the simulated patient, such as, for example, age ranges or medication families.

The control unit 65 communicates with the optical front-end 23 (FIGS. 2 and 3) and the input-output interface 63, as shown. The control unit 65 is used to monitor characteristics of the optical front-end 23 (FIGS. 2 and 3) and to make adjustments that alter a current signal produced by the test unit 12 (FIGS. 1-3). For example, the control unit 65 may include circuitry for measuring light emission characteristics of the light source 61, output current of the detector 18, light transmission properties of the optical device 67, and/or any combination of this these and other suitable factors. The control unit 65 may compare the measured or otherwise obtained information regarding the operation or expected operation of the optical front-end 23 (FIGS. 2 and 3) to ideal characteristics. In certain implementations, the control unit 65 measures a feedback current produced by a photodetector of the optical front-end 23 (FIGS. 2 and 3) and compares a scaled version of the feedback current it to an ideal value of the output current of the test unit 12 (FIGS. 1-3). If there is a difference between the scale feedback current and the idea value, the control unit 65 adjusts a scale factor, a modified scale factor, or a combination of these and other suitable factors. In certain implementations, the control unit 65 measures a current produced by the detector 18 during a first time interval, and the current produced by a secondary detector of optical front-end 23 (FIGS. 2 and 3) during a second time interval. Based on a difference in measured currents, the control unit 65 sets or modifies a scale factor used to produce an updated drive signal that is input to the light source 61 during a third time interval.

In certain implementations, encoder 42 contains information about the optical front-end 23 (FIGS. 2 and 3), such as what type of patient sensor the optical front-end 23 (FIGS. 2 and 3) is intended to simulate (for example, a child or adult sensor, a sensor intended for placement on placement on a forehead or digit, etc.) and/or the wavelengths of light emitted by emitter 61. Encoder 42 may contain information that further specifies characteristics of a simulated patient, such as, for example, the patient's age, weight, and diagnosis. This information may allow the pulse oximetry monitor 14 (FIGS. 1 and 3) to determine, for example, specific threshold ranges and algorithms to be used in computation of simulated physiological parameters. Encoder 42 may, for instance, be a coded resistor which stores values corresponding to the physical properties of the detector 18, the wavelengths of light emitted by the light source 61, and/or a simulated patient's characteristics. In certain implementations, information determined or generated by encoder 42 may be delivered to the decoder 74 via the input-output interfaces 63 and 69, and the received information may be used by the pulse oximetry monitor 14 (FIGS. 1 and 3) to select appropriate algorithms, lookup tables and/or calibration coefficients stored in the pulse oximetry monitor 14 (FIGS. 1 and 3) for calculating a simulated patient's physiological parameters.

In the embodiment shown, the pulse oximetry monitor 14 (FIGS. 1 and 3) includes the microprocessor 48 connected to an internal bus 50. The microprocessor 48 may be adapted to execute software, which may include an operating system and one or more applications, as part of performing the functions described herein. Also connected to bus 50 is a read-only memory (ROM) 52, a random access memory (RAM) 54, user inputs 56, the display 20 (FIGS. 1 and 3), and the speaker 22 (FIGS. 1 and 3). A RAM 54 and the ROM 52 are illustrated by way of example, and not limitation. Any suitable computer-readable media may be used in the system for data storage. Computer-readable media are capable of storing information that may be interpreted by the microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store the desired information and which may be accessed by components of the system.

In the embodiment shown in FIG. 3, a time processing unit (TPU) 58 provides timing control signals to a light drive circuitry 60, which controls when one or more emitters of the light source 61 are illuminated. In certain implementations, the TPU 58 also controls the gating-in of signals from the detector 18 through the amplifier 62 and a switching circuit 64. The received signal from the detector 18 is passed through an amplifier 66, a low pass filter 68, and an analog-to-digital converter 70. The digital data may then be stored in a queued serial module (QSM) 72 (or buffer) for later downloading to the RAM 54 as the QSM 72 fills up. In certain embodiments, there are multiple separate parallel paths having the amplifier 66, the low-pass filter 68, and the A/D converter 70 for multiple light wavelengths or spectra received.

In certain implementations, the microprocessor 48 determines simulated patient physiological parameters, such as $SpO_2$ and pulse rate, using various algorithms and/or look-up tables based on the value of the received signals and/or data corresponding to the current signal received from the detector 18.

Figure 4:
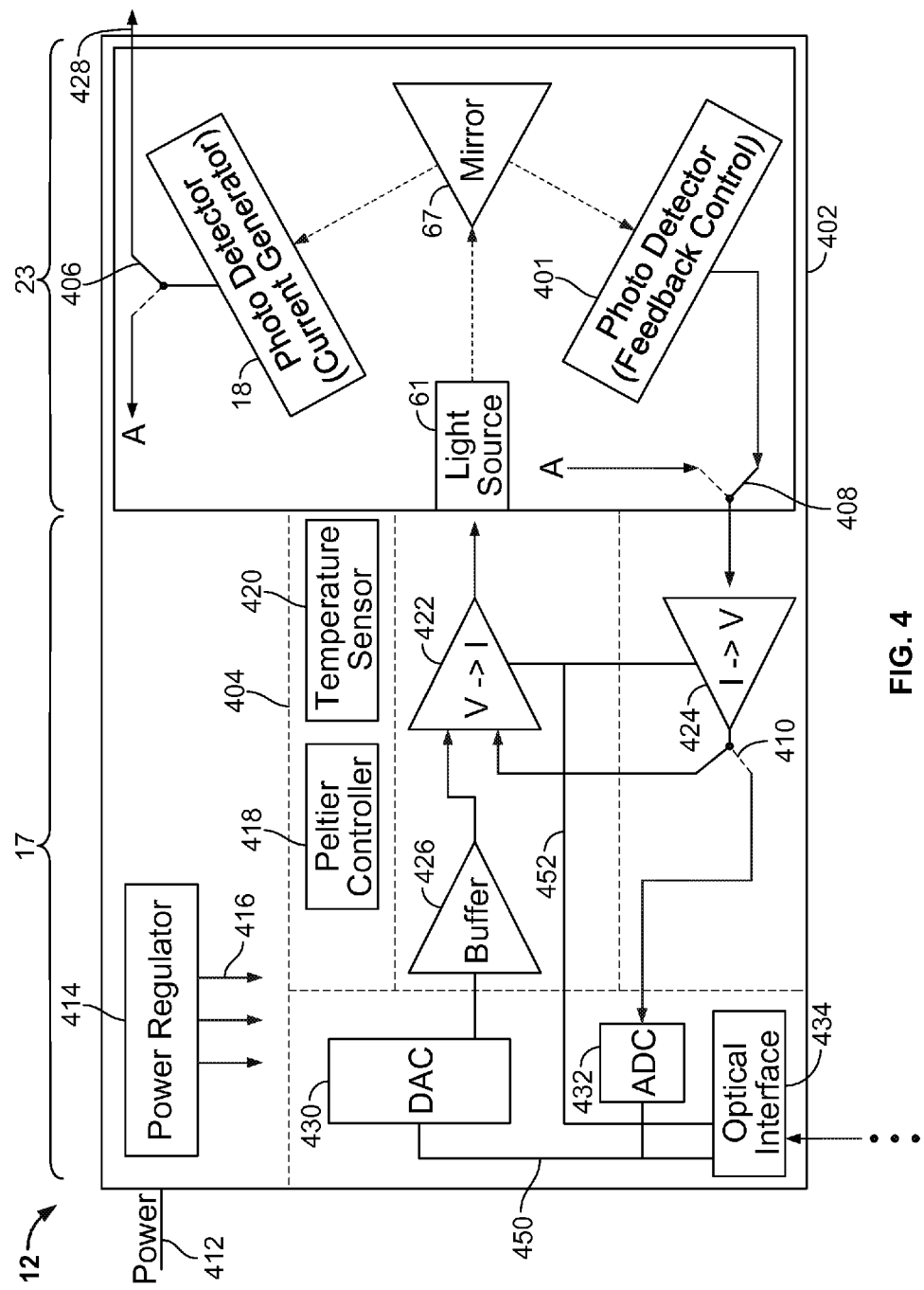
FIG. 4 is an illustrative block diagram of a test control module and an optical front-end configured for producing an output current for testing a test unit.

FIG. 4 is an illustrative block diagram of the control module 17 (FIGS. 2-4) and the optical front-end 23 (FIGS. 2-4), configured for producing an output current for testing the test unit 12 (FIGS. 1-4). Optical front-end 23 (FIGS. 2-4) includes the light source 61 (FIGS. 3 and 4), the detector 18 (FIGS. 3 and 4), and the optical device 67 (FIGS. 3 and 4). As shown in FIG. 4, the optical front-end 23 (FIGS. 2-4) includes two photodetectors. The detector 18 (FIGS. 3 and 4) produces the output current, as described above, while a detector 401 operates within a control loop to produce a feedback current signal that stabilizes the output light intensity of the light source 61 (FIGS. 3 and 4).

During operation of the test unit 12 (FIGS. 1-4), the light source 61 (FIGS. 3 and 4) emits light radiation in pulsed bursts. At least some of the light radiation is reflected by the optical device 67 (FIGS. 3 and 4) to produce incident light on the detectors 18 (FIGS. 3 and 4) and 401. The detectors 18 (FIGS. 3 and 4) and/or 401 may also receive smaller amounts of incident light scattered from other sources within the test unit 12 (FIGS. 1-4), as well as directly from the light source 61 (FIGS. 3 and 4). Current signals are then generated at each of the detectors 18 (FIGS. 3 and 4) and 401 by the photovoltaic effect. In certain implementations, each of the detectors 18 (FIGS. 3 and 4) and 401 are of a same type (such as the same model type or material specifications), as this results in a feedback current signal produced by the detector 401 that more closely resembles the current signal produced by the detector 18 (FIGS. 3 and 4). If a switch 406 is in the right position (as shown in FIG. 4) and a switch 408 is in the down position (as shown in FIG. 4), then the current signal produced by the detector 18 (FIGS. 3 and 4) is output via a current source output 428. In certain implementations, the current source output 428 is provided to the amplifier 62 (FIG. 3). In certain implementations, the current source output 428 is provided to the pulse oximetry monitor 14 (FIGS. 1 and 3) via the input-output interface 63 (FIG. 3).

The output light intensity of the light source 61 (FIGS. 3 and 4) for a given input level may vary over time due to thermal, electrical, and/or ageing effects. Despite these variations, the test unit 12 (FIGS. 1-4) produces a steady output current via the current source output 428 that simulates the current output of an actual patient sensor used in the pulse oximetry system 10 (FIG. 1). To do so, the test unit 12 (FIGS. 1-4) cycles between a current generation mode, during which an output current is provided via the current source output 428, and two control (or learning) modes, referred to as a calibration mode and a feedback mode. The test unit 12 (FIGS. 1-4) operates a majority of the time in the current generation mode. In certain implementations, the operation of the calibration mode is performed relatively infrequently, and as an "outer iteration" of an overall control operation, while the feedback operation is performed more frequently, and as an "inner iteration" of the overall control operation. In another implementation, the feedback operation is performed concurrently with the current generation mode.

During operation in the calibration mode, which will be further described below, the test unit 12 (FIGS. 1-4) drives the light source 61 (FIGS. 3 and 4) using an input drive signal (in either a continuous or pulsed burst) and measures a current produced at the detector 18 (FIGS. 3 and 4) during a first time interval and a current produced by the detector 401 during a second time interval in response to the input drive signal provided to light source 61 (FIGS. 3 and 4). These current signals measured during the first and second time intervals are provided from the optical front-end 23 (FIGS. 2-4) to the control module 17 (FIGS. 2-4) via the switch 408. The relative amplitude levels of the currents measured during the first time interval and second time interval are used by the test unit 12 (FIGS. 1-4) to derive and store a predetermined scale factor.

During operation in the feedback mode, which will be further described below, the test unit 12 (FIGS. 1-4) measures the current produced by the detector 401 during a third time interval (which may be concurrent or partially concurrent with the current generation mode) as a feedback signal determine a modified scale factor that is applied to a transconductance amplifier 422 to control the light intensity produced by the light source 61 (FIGS. 3 and 4). In particular, an optical interface 434 calculates or receives a calculation of the modified scale factor based, at least in part, on the stored predetermined scale factor and the current measured during the third time interval. The modified scale factor is then applied to a signal waveform simulating a PPG signal to produce an updated drive signal for the light source 61 (FIGS. 3 and 4). The modified scale factor is set to a value that, when the updated drive signal using the modified scale factor is applied as input to the light source 61 (FIGS. 3 and 4), results in a current at the detector 18 (FIGS. 3 and 4) during a fourth time interval that has an amplitude and noise characteristics that simulate the current of an actual patient sensor used in the pulse oximetry system 10 (FIG. 1). The modified scale factor is also referred to as a "gain" or "gain factor" herein.

During operation in the current generation mode, which will be further described below, the switch 408 is in the down position (as shown in FIG. 4), a switch 410 is in the up position (as shown in FIG. 4), and the switch 406 is in the right position (as shown in FIG. 4). In this mode, the feedback current signal from the detector 401 is provided to a transimpedance amplifier 424. The transimpedance amplifier 424 is a current-controlled voltage source with an output provided to the transconductance amplifier 422, and the transconductance amplifier 422 is a voltage-controlled current source that outputs a current determined by the input drive signal applied to the transconductance amplifier 422 and the modified scale factor determined during a most recent feedback mode operation of the test unit 12 (FIGS. 1-4). In particular, in the current generation mode, the transconductance amplifier 422 outputs a current signal based on the relation $$I_{out} = V_{in} \times g,$$

where $V_{in}$ an input voltage applied to the transconductance amplifier 422, and where g is the modified scale factor determined during the most recent feedback mode operation. The light source 61 (FIGS. 3 and 4) receives $I_{out}$ as a drive signal, and emits light accordingly. A current is produced by the detector 18 (FIGS. 3 and 4) in response to the emission of light from the light source 61 (FIGS. 3 and 4), and this current is provided as a test current via the current source output 428.

When the test unit 12 (FIGS. 1-4) operates in the feedback mode, the switch 408 is in the down position (as shown in FIG. 4) and the switch 410 is in the down position (not shown in FIG. 4). Thus, the output of the transimpedance amplifier 424 is provided to an analog-to-digital converter 432. The output of the analog-to-digital converter 432 is then provided to the optical interface 434 via a line 450, which may correspond to a serial-to-parallel interface. The optical interface 434 determines an updated value of the modified scale factor g needed to keep the output current of the transconductance amplifier 422 constant (so that the current provided via current source output 428 during a subsequent current generation mode operation of the test unit 12 (FIGS. 1-4) remains constant). In particular, the optical interface 434 determines the updated value of the modified scale factor g based, at least in part, on a predetermined scale factor determined during a previous calibration mode operation of the test unit 12 (FIGS. 1-4) and the input received from the analog-to-digital converter 432. The updated value of the modified scale factor g is provided to the transconductance amplifier 422 via a line 452. In addition, the optical interface 434 provides a signal waveform simulating a PPG signal produced by an optical patient sensor via the line 450 to a digital-to-analog converter 430. This signal waveform is then passed to a buffer 426 and applied to the transconductance amplifier 422. The buffer 426 provides a time delay between input and output that ensures that by the time the output signal of the buffer 426 arrives at the transconductance amplifier 422, the updated modified scale factor g has been set at the transconductance amplifier 422. This, in turn, ensures that output current of the transconductance amplifier 422 is at the desired level.

When the test unit 12 (FIGS. 1-4) operates in the calibration mode, the switch 410 is in the down position (as shown in FIG. 4), and the switch 406 is in the left position (not shown in FIG. 4). During an initial time period of the calibration mode, the switch 408 is in the up position (not shown in FIG. 4). During this initial time period, a current produced by the detector 18 (FIGS. 3 and 4) is provided to the optical interface 434 via the transimpedance amplifier 424 and the analog-to-digital converter 432. During a subsequent time period of the calibration mode, the switch 408 is moved to the down position (as shown in FIG. 4), while the switch 410 is maintained in the down position (as shown in FIG. 4), and the switch 406 is maintained in the left position (not shown in FIG. 4). During this subsequent time period, a current produced by the detector 401 is provided to the optical interface 434 via the transimpedance amplifier 424 and the analog-to-digital converter 432. The optical interface 434 then measures the current signal received in the initial time period and the subsequent time period of the calibration mode, and derives a predetermined scale factor. In certain implementations, the optical interface 434 derives the predetermined scale factor by dividing an average current level measured during the initial time period of the calibration mode with the average current level measured during the subsequent time interval. The test unit 12 (FIGS. 1-4) then stores the value of the predetermined scale factor.

The test unit 12 (FIGS. 1-4) is designed to produce a low-noise current output (for example, having an AC noise component of less than a root mean square value of about 50 pA). However, the current signal output by the detector 18 (FIGS. 3 and 4) may be degraded by noise. One source of noise is ambient light that reaches the light detector. Another source of noise is electromagnetic coupling from other electronic instruments. Noise in a current signal produced by the detector 18 (FIGS. 3 and 4) may impair the ability of the test unit 12 (FIGS. 1-4) to determine whether the pulse oximetry system 10 (FIG. 1) is functioning properly. For example, noise in the output current of the detector 18 (FIGS. 3 and 4) could reduce the accuracy of simulated physiological parameters, such as a simulated pulse rate or oxygen saturation level, produced by the pulse oximetry system 10 (FIG. 1). The test unit 12 (FIGS. 1-4) may employ one or more of the following techniques to achieve lowered noise levels.

One technique includes limiting the magnitude of the modified scale factor (that is, values of g) by maximizing a fraction of light emitted by the light source 61 (FIGS. 3 and 4) that is incident on a detector (for example, either the detector 18 (FIGS. 3 and 4) or the detector 401). In particular, the optical device 67 (FIGS. 3 and 4) includes a prismed mirror that has desirable reflectivity properties. Further, the optical device 67 (FIGS. 3 and 4) may be constructed from, or coated with, materials designed to maximize reflectivity onto the detector 18 (FIGS. 3 and 4) and the detector 401. By receiving a large amount of light reflected from the optical device 67 (FIGS. 3 and 4), the test unit 12 (FIGS. 1-4) may have a lower amplification requirement when generating small DC currents (for example, 100 pA or less) and therefore introduce less electrical noise into current provided via the current source output 428.

In another technique, the test unit 12 (FIGS. 1-4) uses an external module shield 402, placed around one or more interior or exterior surfaces of the test unit 12 (FIGS. 1-4) and an internal shielding boundaries 404 (indicated by the dashed non-directional lines in FIG. 4). For example, each of the external module shield 402 and the internal shielding boundaries 404 may be constructed from sheet metal, metal screen, and/or metal foam. Additionally or alternatively, portions of the test unit 12 (FIGS. 1-4) may be coated with a metallic ink containing one or more suitable metals, including copper, nickel, and/or any other suitable shielding material.

Further, to ensure consistent and uninterrupted operation of the light source 61 (FIGS. 3 and 4) (and the test unit 12 (FIGS. 1-4) generally), the test unit 12 (FIGS. 1-4) may control the power received via a line 412 using a power regulator 414. In particular, the power regulator 414 includes a power supply unit (PSU) for converting a general-purpose AC input into a DC current. The power regulator 414 performs regulation and/or filtering of the input power provided by the line 412 to produce a consistent and low-noise output power signal. The output power signal is provided to components of the test unit 412 via power lines 416.

It will be understood that although FIG. 4 depicts switches 406, 408, and 410 as physical switches, these depictions are meant only to illustrate the logical operation of the test unit 12 (FIGS. 1-4). In a suitable implementation, any combination of switches 406, 408, and 410 may be implemented as hardware switches, software switches, using circuitry that mimics the operation of a switch, and/or by any other suitable technique that produces a logical behavior of a switch. Further, it will be understood that although the optical front-end 23 (FIGS. 2-4) is depicted as including a single light source, a suitable implementation of the optical front-end 23 (FIGS. 2-4) may include multiple light sources.

It will be understood that, in certain implementations, the optical device 67 (FIGS. 3 and 4) is adjustable within the test unit 12 (FIGS. 1-4) and that the fraction of light emitted by the light source 61 (FIGS. 3 and 4) incident on each of the detectors 18 (FIGS. 3 and 4) and 401 may be changed as a result. For example, a relative position and/or orientation of the optical device 67 (FIGS. 3 and 4) is adjusted, through automatic or manual means. Both the aggregate amount of light and the relative fraction of light falling on each detector may be controlled by adjusting the position and/or orientation of the optical device 67 (FIGS. 3 and 4). Further, the orientation and/or position of one or both of the detectors 18 (FIGS. 3 and 4) and 401 may be adjustable.

The test unit 12 (FIGS. 1-4) includes a temperature sensor 420 and a temperature controller 418 to keep the operating temperature of the test unit 12 (FIGS. 1-4) relatively steady. The temperature controller 418 may regulate an internal temperature of the test unit 12 (FIGS. 1-4) based on temperature readings provided by the temperature sensor 420. The temperature controller 418 may be, for example, a Peltier controller. In certain implementations, the temperature controller 418 is preprogrammed within an ideal target temperature via a programmable port (not shown). The target temperature may be specified in absolute terms (for example, a certain number of degrees) or in relative terms (for example, relative to the ambient air temperature). The Peltier controller 418 may control or modulate the temperature of the test unit 12 (FIGS. 1-4) by generating a temperature difference across two sides of the temperature controller 418, thus transferring heat across a temperature gradient. In some implementations, the test unit does not include a temperature sensor or a temperature controller. In some implementations, the temperature controller 418 holds the operating temperature of one or more components of the test unit 12, such as the light source 61 or the photodetectors 18 or 401, at a relatively constant value, thereby reducing thermally-induced drift in the output current 428. In some implementations, the temperature controller 418 holds the operating temperature of one or more components of the test unit 12 at a temperature below ambient temperature, thereby reducing thermally-generated noise in the output current 428.

Figure 5:
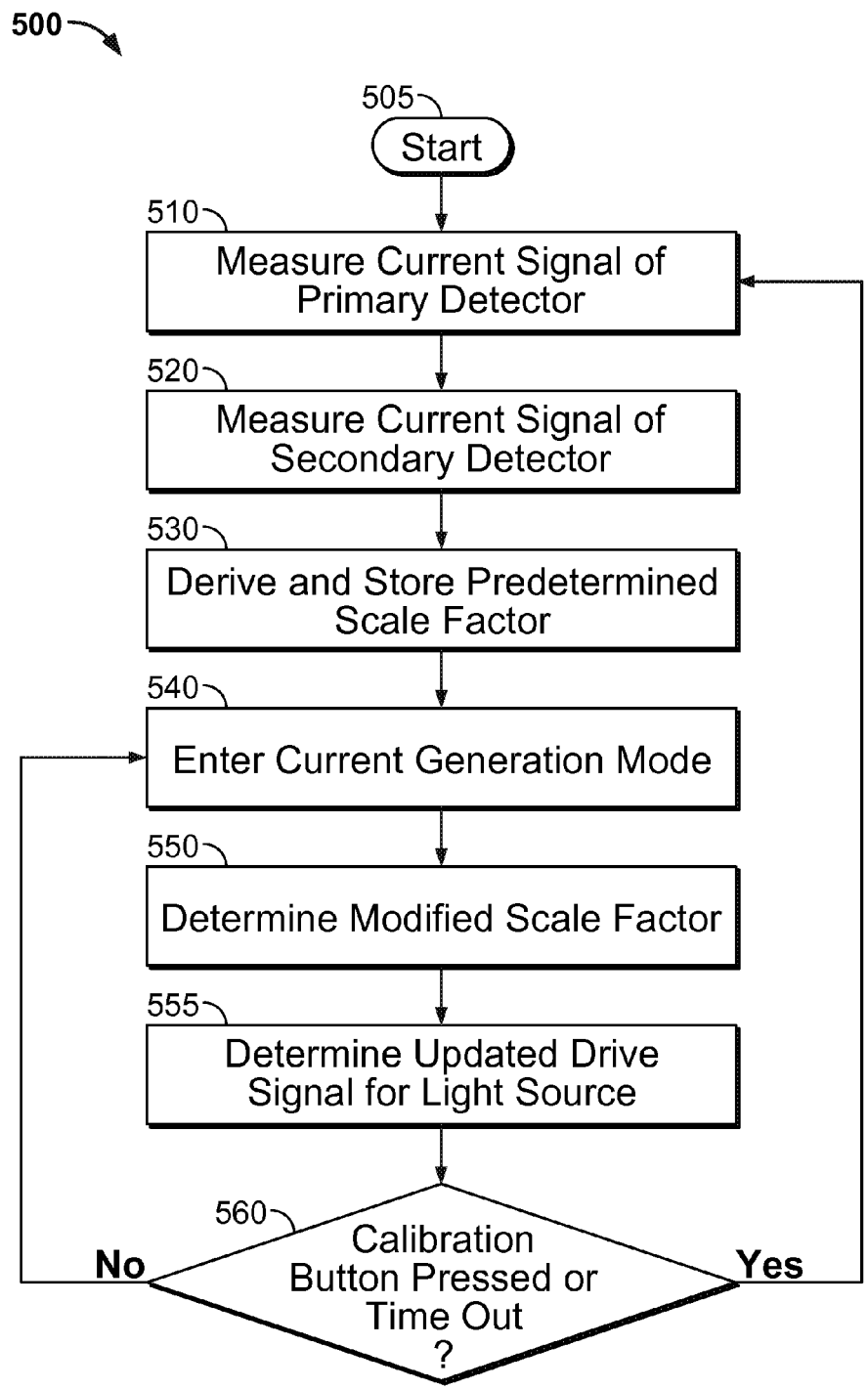
FIG. 5 is a flow chart of illustrative steps of a process performed by a test unit to cycle among calibration, current generation, and feedback modes.

FIG. 5 is a flow chart of illustrative steps of a process performed by the test unit 12 (FIGS. 1-4) to cycle among the calibration mode, current generation mode, and feedback mode. A process 500 operates in the calibration mode in steps 510, 520, and 530, during which a predetermined scale factor is derived and stored based on current measurements made at the detectors 18 (FIGS. 3 and 4) and 401 (FIG. 4). The process 500 operates in the current generation mode at the step 540, during which a current output is provided via the current source output 428 (FIG. 4). The process 500 operates in the feedback mode at the steps 550 and 555, during which a modified scale factor is calculated and an updated drive signal for the light source 61 (FIGS. 3 and 4) is determined. As shown in FIG. 5, the test unit 12 (FIGS. 1-4) operates in an inner iteration between the current generation mode and the feedback mode (the steps 540, 550, and 555), and operates in an outer iteration in the calibration mode the steps 510, 520, and 530).

Test unit 12 (FIGS. 1-4) may initiate the process 500 automatically at set times (including at a time that the test unit 12 (FIGS. 1-4) first initializes) and/or the process 500 may be user initiated. User initiation of the process 500 may be performed via the calibration button 19 (FIG. 2) and/or by inputting commands to the pulse oximetry monitor 14 (FIGS. 1 and 3) and/or the multi-parameter patient monitor 26 (FIG. 1).

The process 500 begins at the step 505 in response to a timer output or a power up of the test unit 12 (FIGS. 1-4). At the step 510, the test unit 12 (FIGS. 1-4) enters a calibration mode. The test unit 12 (FIGS. 1-4) measures a current signal of a primary detector during a first interval. At the step 510, the switch 410 (FIG. 4) is in the down position (as shown in FIG. 4), and the switch 406 (FIG. 4) is in the left position (not shown in FIG. 4). The test unit 12 (FIGS. 1-4) measures a current produced by the detector 18 (FIGS. 3 and 4), and the measured current is provided to the optical interface 434 (FIG. 4) via the transimpedance amplifier 424 (FIG. 4) and the analog-to-digital converter 432 (FIG. 4).

At the step 520, the test unit 12 (FIGS. 1-4) measures a current signal of a secondary detector during a second time interval. At the step 520, the switch 408 (FIG. 4) is moved to the down position (as shown in FIG. 4), while the switch 410 (FIG. 4) is maintained in the down position (as shown in FIG. 4), and the switch 406 (FIG. 4) is maintained in the left position (not shown in FIG. 4). The test unit 12 (FIGS. 1-4) measures a current produced by the detector 401 (FIG. 4), and the measured current is provided to the optical interface 434 (FIG. 4) via the transimpedance amplifier 424 (FIG. 4) and the analog-to-digital converter 432 (FIG. 4).

At the step 530, the test unit 12 (FIGS. 1-4) derives a predetermined scale factor based on the amplitude levels of the currents measured at the steps 510 and 520. In certain implementations, the test unit 12 (FIGS. 1-4) determines the predetermined scale factor by forming a ratio between the average current level received at the step 510 and the average current level received at the step 520. In certain implementations, the test unit 12 (FIGS. 1-4) received the predetermined scale factor from the optical interface 434 (FIG. 4).

At the step 540, the test unit 12 (FIGS. 1-4) operates according to the current generation mode. The switch 408 (FIG. 4) is in the down position (as shown in FIG. 4), the switch 410 (FIG. 4) is in the up position (as shown in FIG. 4), and the switch 406 (FIG. 4) is in the right position (as shown in FIG. 4). In this mode, the transconductance amplifier 422 (FIG. 4) outputs a current determined by an input voltage applied to the transconductance amplifier 422 (FIG. 4) and the modified scale factor determined during a most recent feedback mode operation to the light source 61 (FIGS. 3 and 4). A current is produced by the detector 18 (FIGS. 3 and 4) in response to the emission of light from the light source 61 (FIGS. 3 and 4), and this current is provided as a test current via the current source output 428 (FIG. 4).

At the step 550, the test unit 12 (FIGS. 1-4) enters the feedback mode. In this mode, the switch 408 (FIG. 4) is in the down position (as shown in FIG. 4) and the switch 410 (FIG. 4) is in the down position (not shown in FIG. 4). In this mode, the output of the transimpedance amplifier 424 (FIG. 4) is provided to the optical interface 434 (FIG. 4) via the analog-to-digital converter 432 (FIG. 4). In certain implementations, the optical interface 434 (FIG. 4) receives a modified scale factor based, at least in part, on the output of the transimpedance amplifier 424 (FIG. 4) and the stored value of the predetermined scale factor. In certain implementations, the test unit 12 (FIGS. 1-4) computes the value of the modified scale factor based, at least in part, on the output of transimpedance amplifier and the stored value of the predetermined scale factor. In certain implementations, the modified scale factor is determined to be a value that maintains an intensity of light emitted from the light source 61 (FIGS. 3 and 4) constant, so that a current provided via the current source output 428 (FIG. 4) during a subsequent current generation mode operation of the test unit 12 (FIGS. 1-4) remains constant. In certain implementations, the modified scale factor is determined based on a direct measurement of the current produced by the detector 18 (FIGS. 3 and 4), while in other implementations it is determined indirectly based, at least in part, on the predetermined scale factor and the output of the transimpedance amplifier 424 (FIG. 4).

At the step 555, the optical interface 434 (FIG. 4) provides a signal waveform simulating a PPG signal produced by an optical patient sensor via the line 450 (FIG. 4) to the digital-to-analog converter 430 (FIG. 4). The signal waveform is then passed to the buffer 426 (FIG. 4) and provided to the transconductance amplifier 422 (FIG. 4). Further, the modified scale factor determined at the step 550 is applied to the transconductance amplifier 422 (FIG. 4), and the output of the transconductance amplifier 422 (FIG. 4) is a modified signal waveform.

In certain implementations, the transconductance amplifier 422 (FIG. 4) scales the signal waveform uniformly by a factor corresponding to the value of the modified scale factor to produce the modified signal waveform. The modified signal waveform is then provided to the light source 61 (FIGS. 3 and 4) as an updated drive signal. In certain implementations, the buffer 426 (FIG. 4) provides a time delay between input and output that ensures that by the time the output signal of the buffer 426 (FIG. 4) arrives at the transconductance amplifier 422 (FIG. 4), the modified scale factor has been provided to the transconductance amplifier 422 (FIG. 4). This, in turn, ensures that output current of the transconductance amplifier 422 (FIG. 4) is at the desired level.

At the step 560, the process 500 may continue iterating between the steps 540 and 550, where the detector 18 (FIGS. 3 and 4) acts as a current source and small changes (or updates) to the value of the modified scale factor are occasionally made, or returns to the step 510, so that the test unit 12 (FIGS. 1-4) may once again enter the calibration mode. At the step 560, the test unit 12 (FIGS. 1-4) determines whether the calibration button 19 (FIG. 2) has been pressed and/or whether the iteration between the steps 540 and 550 has run for enough time (for example, for a long enough period of time or for enough iterations). If either of these conditions are met, then the process 500 returns to the step 510. Otherwise, the process 500 continues to the step 540.

Figure 6:
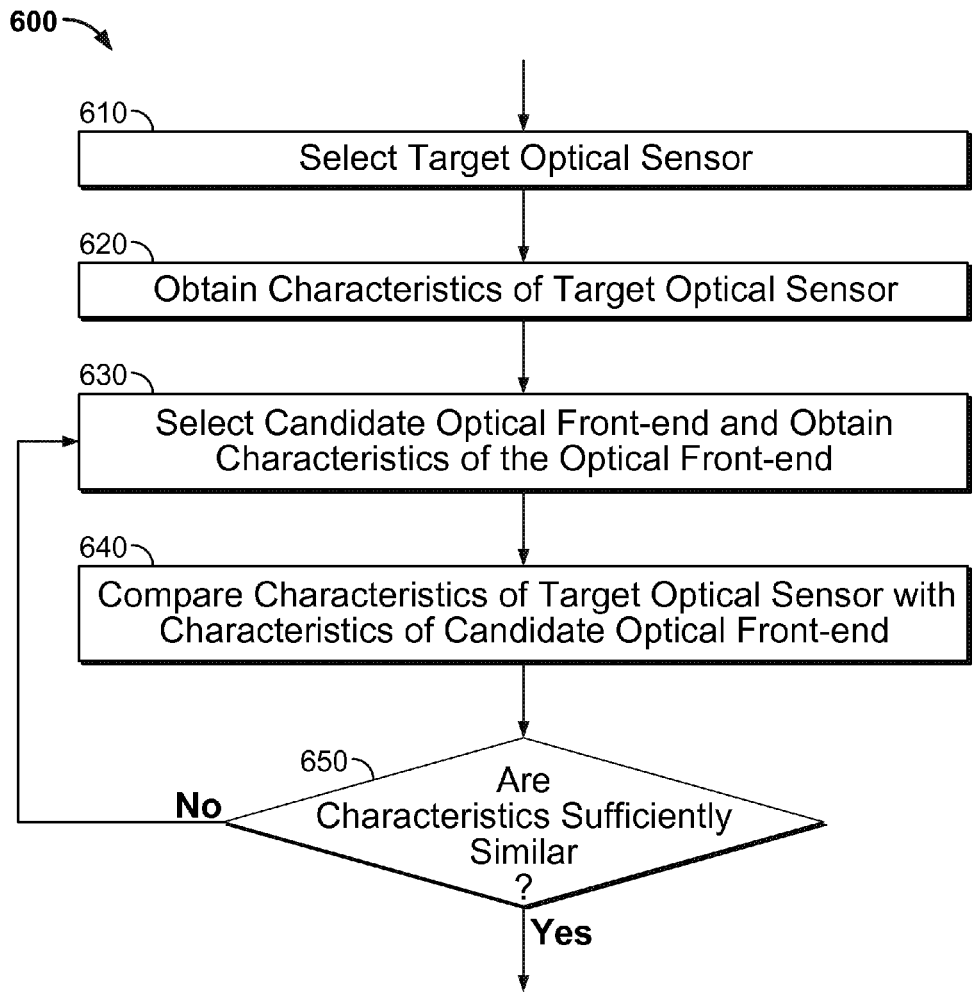
FIG. 6 is a flow chart of illustrative steps of a process used to determine components of a test unit.

FIG. 6 is a flow chart of illustrative steps of a process used to determine components of a the test unit 12 (FIGS. 1-4). A process 600 may be implemented by the pulse oximetry system 10 (FIG. 1), for example, by the pulse oximetry monitor 14 (FIGS. 1 and 3) and/or the multi-parameter patient monitor 26 (FIG. 1). Alternatively, the process 600 may be performed by another hardware-based or other testing system (not pictured in FIG. 1).

At the step 610, the process 600 selects a target optical sensor that the test unit 12 (FIGS. 1-4) is intended to simulate. For example, various sensors used by the pulse oximetry system 10 (FIG. 1) may be designed for neonates, children, and adults, and/or may be configured to operate on different parts of the body. One of these sensor types is chosen at the step 610, for example, using the user inputs 56 (FIG. 3) or another hardware-based selection method. At the step 620, characteristics of the optical sensor chosen at the step 610, such as a light intensity level produced by the optical sensor or a wavelength spectrum of the optical sensor, are determined. Characteristics may be retrieved from a preexisting template (for example, stored in the ROM 52 (FIG. 3) and/or the RAM 54 (FIG. 3)) or determined in real-time. Characteristics may also be supplied by a manufacturer as part of a device specification, and may correspond to the nominal characteristics of a batch or group of similarly-manufactured devices. Characteristics determined at the step 620 may include both electrical and optical characteristics of a detector and one or more emitters employed by the target optical sensor. Characteristics determined at the step 620 may include a detector current output level, electrical noise-levels, a LED emitter emission spectrum, one or more circuit response times, and/or any suitable combination of these and other characteristics.

At the step 630, a candidate optical front-end is selected. The candidate optical front-end is an optical front-end that will be evaluated for inclusion in the test unit 12 (FIGS. 1-4). In certain implementations, the candidate optical front-end is an entire pre-existing optical front-end module. In certain implementations, one or more components of a optical front-end (for example, detector and/or light source elements) is selected as the candidate optical front-end. Selection of the candidate optical front-end is made via the user inputs 56 (FIG. 3) or by any other suitable selection mechanism. The characteristics of the candidate optical front-end are obtained at the step 630. In certain implementations, one or more of the characteristics described in relation to FIG. 8 (optical characteristics) and FIG. 9 (detector characteristics) are obtained. These characteristics may be determined in real-time or retrieved from existing data related to the candidate optical front-end.

At the step 640, characteristics of the target optical sensor determined at the step 620 are compared to characteristics of the candidate optical front-end selected at the step 630. In certain implementations, a difference between a characteristic of the target optical sensor (e.g., a light intensity value) and the candidate optical front-end is quantified by a metric value (e.g., the difference in the light intensity values) for each characteristic determined at 620. The set of characteristics relevant to the comparison of step 640 may be referred to as a "characteristic profile."

At the step 650, it is determined if characteristics of the target optical sensor determined at the step 620 are sufficiently similar to those of the candidate optical front-end selected at the step 630. In certain implementations, one or more metrics determined at the step 640 are linearly weighed to produce a single overall metric value. This metric value is then compared to a threshold value at the step 650 to determine if characteristics of the target optical sensor determined at the step 620 are sufficiently similar to those of the candidate optical front-end selected at the step 630. In certain implementations, the target optical sensor and the candidate optical front-end are considered sufficiently similar if they are manufactured according to the same manufacturing processes, by the same manufacturer, according to the same specifications, within a same manufacturing batch, or a combination thereof. If the characteristics are sufficiently close (e.g., within a tolerance), the process 600 continues. Otherwise, the process 600 returns to the step 630, where a new candidate optical front-end is selected.

Figure 7:
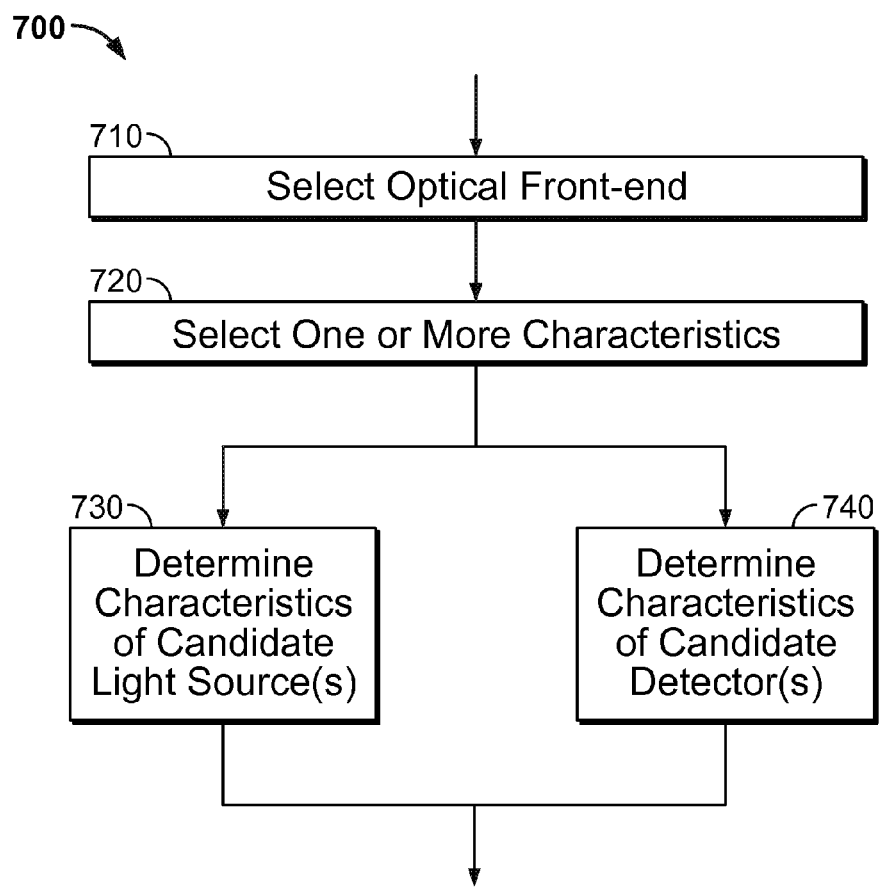
FIG. 7 is a flow chart of illustrative steps of a process used to determine characteristics of an optical front-end.

FIG. 7 is a flow chart of illustrative steps of a process used to determine characteristics of an optical front-end. A process 700 may correspond to a more detailed version of the step 630 (FIG. 6). The process 700 may be implemented by the pulse oximetry system 10 (FIG. 1), for example, by the pulse oximetry monitor 14 (FIGS. 1 and 3) and/or the multi-parameter patient monitor 26 (FIG. 1). Alternatively, the process 700 may be performed by another hardware-based or other testing system (not pictured in FIG. 1).

At the step 710, the process 700 selects a candidate optical front-end. At the step 720, the process 700 selects one or more characteristics used to determine if the target optical sensor determined at the step 620 (FIG. 6) is sufficiently similar to the candidate optical front-end selected at the step 630 (FIG. 6). In certain implementations, the number and type of characteristics selected at the step 720 is based, at least in part, on an accuracy with which the candidate optical front-end is to match the target optical sensor and/or the number of candidate optical front-end designs available. At the step 730, characteristics of a candidate light source (for example, the light source 61 (FIGS. 3 and 4)) may be determined. In particular, the characteristics determined at the step 730 may correspond to those characteristics selected at the step 720 that pertain to light emission. At the step 740, characteristics of a candidate detector (for example, the detector 18 (FIGS. 3 and 4)) are determined. The characteristics determined at the step 740 correspond to those characteristics selected at the step 720 that pertain to detector properties.

FIG. 8 is a flow chart of illustrative steps of a process used to determine characteristics of a candidate light source for inclusion in an optical front-end. A process 800 may correspond to a more detailed version of the step 730 (FIG. 7). The process 800 may be implemented by one or more components of the pulse oximetry system 10 (FIG. 1), for example, by the pulse oximetry monitor 14 (FIGS. 1 and 3) and/or the multi-parameter patient monitor 26 (FIG. 1). Alternatively, the process 700 may be performed by another hardware-based or other testing system (not pictured in FIG. 1).

At the step 810, an intensity level of the candidate light source is determined. For example, one or more lux values (that is, measurements of luminous power per area) may be determined corresponding the candidate light source. At the step 820, a propagation direction and dispersion of the candidate light source is determined. The determined radiation pattern may include data related to a power fall-off of the candidate light source versus angular measurements. Summary information regarding the propagation pattern and/or dispersion of the candidate light source may be determined. For example, it may be determined that the candidate light source produces a pattern that is either more direct or point-like. Additionally or alternatively, a directional spreading factor may be determined.

At the step 830, a wavelength spectrum generated by the candidate light source may be determined. In certain implementations, values of radiation emitted by the candidate light source versus frequency are determined within a frequency range of interest. For example, a color rendering index and/or a value summarizing the spectral peakedness is determined. At the step 840, a polarization associated with the candidate light source may be determined. Polarization may be determined in terms of an orientation of the light source's electric field at a point in space over a period of oscillation. Summary information regarding polarization of the candidate light source may be determined. For example, it may be determined if the polarization of the candidate light source is roughly linear, circular, or elliptical.

At the step 850, longevity, reliability and/or other long-term characteristics of the candidate light source are determined. Such characteristics may include an average lamp life of the candidate light source (for example, measured in hours). Reliability characteristics of the candidate light source may also be determined. Such reliability characteristics may include an average probability of outage versus service lifetime may be determined. At the step 860, efficiency and power requirements of the candidate light source are determined. The efficiency of the candidate light source may be expressed in terms of one or more lumens per watt values. Further, the power requirements and/or specification of the candidate light source may determined. For example, a minimum current and/or voltage level required to turn on the candidate light source may be determined. Similarly, a maximum specified current and/or voltage level for which the candidate light source is compliant may be determined.

At the step 870, noise and/or spurious transmission produced by the candidate light source are determined. The determined data may be in the form of statistical data (for example, a relative frequency and power distribution of the unintended noise spectra introduced by the candidate light source). Alternatively or additionally, a fraction of power emitted from the candidate light source due to noise and/or spurious components may be determined.

It will be understood that one or more of the steps used to determine characteristics shown in FIG. 8 may be omitted, and/or other steps used to determine additional characteristics may be added. Further, it will be understood that the order of the steps displayed in FIG. 8 may be rearranged and/or that some or all of the steps displayed in FIG. 8 may be performed in a parallel fashion. Further, it will be understood that some or all of the determinations made in the steps of FIG. 8 may be performed based on a single or multiple measurements taken at different times and/or under different operating conditions. For example, the multiple measurements may be averaged to form a single measurement or determination.

Further, it will be understood that some or all of the measurements performed in the steps of FIG. 8 may be performed by first situating the candidate light source within the test unit 12 (FIGS. 1-4) or a configuration that approximates the configuration of the test unit 12 (FIGS. 1-4) and that some or all of the measurements performed in the steps of FIG. 8 may be performed prior to and/or after light is reflected by an optical device (for example, the optical device 67 (FIGS. 3 and 4) of the test unit 12 (FIGS. 1-4). In particular, performing measurements of the steps of FIG. 8 after reflection by an optical device may provide a more accurate assessment of the characteristics of the candidate light source as they effect the operation of the optical front-end 23 (FIGS. 2-4). It will be understood that one or more of the characteristics determined in the steps of FIG. 8 may be performed as a function of the lifetime of the candidate light source. For example, if the candidate light source has an average lifetime of 1000 hours, the process 800 may be repeated every 100 hours.

FIG. 9 is a flow chart of illustrative steps of a process used to determine characteristics of a candidate detector for inclusion in an optical front-end. A process 900 may correspond to a more detailed version of the step 740 (FIG. 7). The process 900 may be implemented by one or more components of the pulse oximetry system 10 (FIG. 1), for example, by the pulse oximetry monitor 14 (FIGS. 1 and 3) and/or the multi-parameter patient monitor 26 (FIG. 1). Alternatively, the process 900 may be performed by another hardware-based or other testing system (not pictured in FIG. 1).

At the step 910, noise and/or other corruptive effects in the electrical current output produced by the candidate detector are determined. For example, the effect of ambient noise, noise due to electrical coupling, and/or an overall signal-to-noise ratio for the candidate detector is determined. At the step 920, an efficiency of the candidate detector in absorbing incoming photons may be determined. This efficiency may be expressed as a percentage of photons absorbed and may be referred to as a quantum efficiency of the detector. The efficiency of the detector may depend on a wavelength spectrum of a candidate light source.

At the step 930, a sensitivity of the detector is determined. For example, a current generated by the detector per watt of incident (that is, absorbed) optical power is determined. The sensitivity may depend on a wavelength spectrum of a candidate light source. At the step 935, a spectral response of the detector is determined. For example, the relative currents generated by the detector (indicative of the relative detection efficiency) in response to incident light of different wavelengths are determined. At the step 940, linearity of the candidate detector is determined. In certain implementations, a relation between incident energy flux on the candidate detector and an output current level is determined for a range of energy flux values. For example, a deviation from perfectly linear relationship between the incident energy flux and the output current level may be determined (expressed as a percentage) over a certain dynamic operating range of the candidate detector.

At the step 950, longevity, reliability or other long-term characteristics of the candidate detector are determined. For example, an average lamp life of the candidate detector (measured in hours) may be determined. Reliability characteristics of the candidate detector are determined at the step 950, and may include, for example, an average probability of outage versus service lifetime of the candidate detector. At the step 960, a time constant of the candidate detector is determined. For example, a time delay of the candidate detector between absorption of incident light and production of a full-strength current signal may be measured. Further, a relationship between the strength of an output current signal of the candidate detector (expressed, for example, as a percentage of the full steady-state current value) versus time since incident light first started to be absorbed by the detector may be determined. At the step 970, a leakage current associated with operation of the candidate detector is determined.

It will be understood that one or more of the steps used to determine characteristics shown in FIG. 9 may be omitted, and/or other steps used to determine additional characteristics may be added. Further, it will be understood that the order of the steps displayed in FIG. 9 may be rearranged and/or that some or all of the steps displayed in FIG. 9 may be performed in a parallel structure. Further, it will be understood that some or all of the determinations made in the steps of FIG. 9 may be performed based on a single measurement or multiple measurements taken at different times and/or under different operating conditions. For example, the multiple measurements may be averaged to form a single measurement or determination.

Further, it will be understood that some or all of the measurements performed in the steps of FIG. 9 may be performed by first situating the candidate detector within the test unit 12 (FIGS. 1-4) or a configuration that approximates the configuration of the test unit 12 (FIGS. 1-4). It will be understood that one or more of the characteristics determined in the steps of FIG. 9 may be performed as a function of the lifetime of the candidate light source. For example, if the candidate light source has an average lifetime of 1000 hours, the process 800 (FIG. 8) may be repeated every 100 hours.

Figure 10:
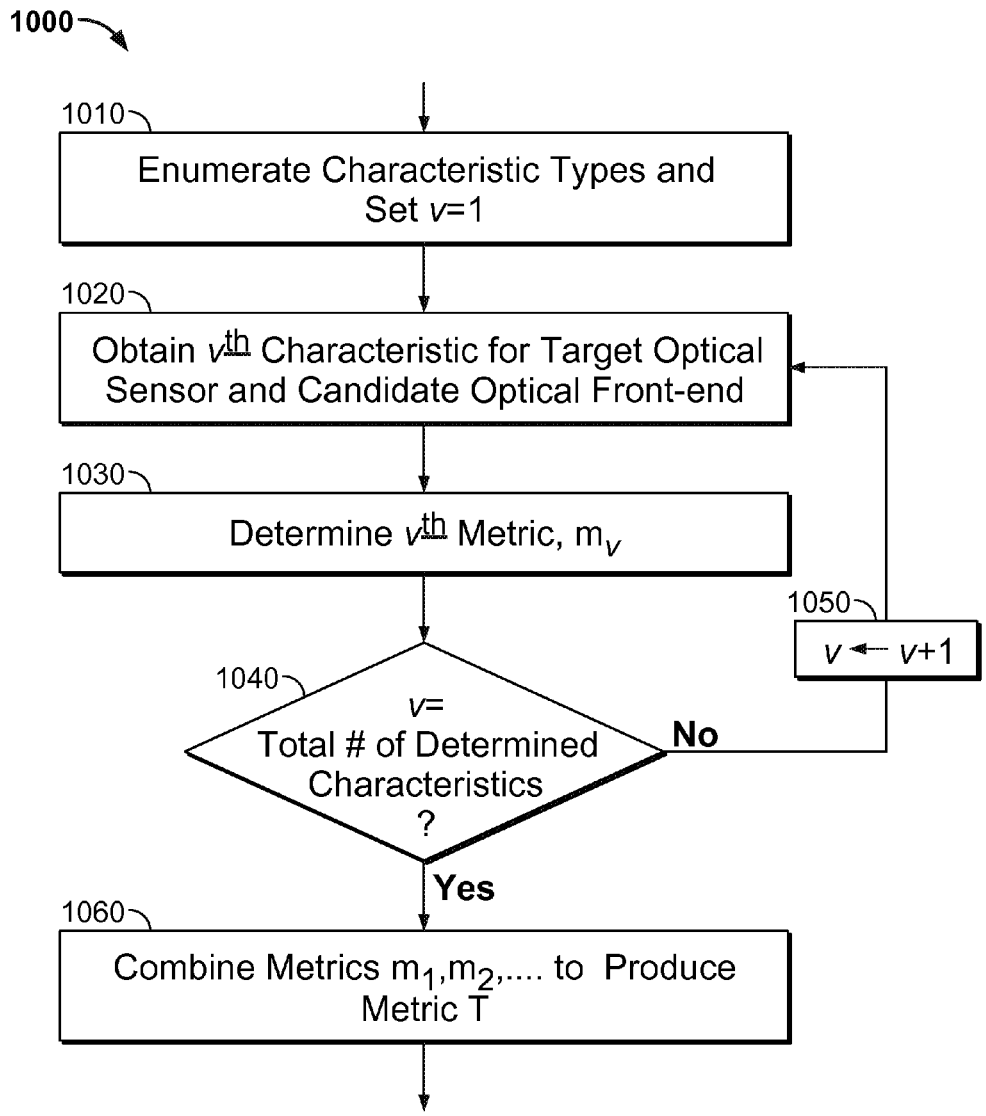
FIG. 10 is a flow chart of illustrative steps of a process used to compare characteristics of a target optical sensor with characteristics of a candidate optical front-end.

FIG. 10 is a flow chart of illustrative steps of a process used to compare characteristics of a target optical sensor with characteristics of a candidate optical front-end. A process 1000 may correspond to a more detailed version of the step 640 (FIG. 6). The process 1000 may be implemented by one or more components of the pulse oximetry system 10 (FIG. 1), for example, by the pulse oximetry monitor 14 (FIGS. 1 and 3) and/or the multi-parameter patient monitor 26 (FIG.

1). Alternatively, the process 1000 may be performed by another hardware-based or other testing system (not pictured in FIG. 1).

At the step 1010, a set of characteristics types to be compared are enumerated as a characteristic profile. For example, a total of M characteristic types may be determined at each of the steps 620 (FIG. 6) (for the target optical sensor) and 630 (FIG. 6) (for the candidate optical front-end). These M characteristic types are enumerated in an order from 1 to M at the step 1010. Further, a counter v may be set to the value 1.

At the step 1020, the $v^{th}$ characteristic for each of the target optical sensor and the candidate optical front-end is obtained. For example, the $v^{th}$ characteristic may correspond to a intensity value of a light source. In this case, the intensity value of a light source used in each of the target optical sensor and the candidate optical front-end is obtained, for example, from the ROM 52 (FIG. 3) and/or the RAM 54 (FIG. 3).

At the step 1030 a metric is formed that summarizes a comparison between the two characteristics for the $v^{th}$ characteristic type determined at the step 1020. For example, each of the two characteristics determined at the step 1020 may be a scalar value, function, a matrix value, and/or any other type of data representation. For example, in certain implementations, each of the two characteristics determined at the step 1020 is a continuous function (for example, a function representing a intensity of a light source versus radial distance). In these implementations, the $v^{th}$ metric corresponds to a ratio of the integral value of one function divided by the other (that is producing a single scalar value). In some implementations, the metric is a binary value representing whether or not one or more particular characteristics of the target optical sensor and the candidate optical front-end fall are within a tolerance range of each other. In some implementations, the metric is a binary value representing whether components of the target optical sensor and the candidate optical front-end are manufactured according to the same manufacturing processes, by the same manufacturer, according to the same specifications, within a same manufacturing batch, or a combination thereof.

At the step 1040, the process 1000 determines if a counter value has reached a number equal to the total number of characteristics to be used in the comparison (for example, the value M). If so, the process 1000 continues to a step 1060. Otherwise, the process 1000 proceeds to a step 1050, where the counter value is incremented by 1, and the process 1000 then returns to the step 1020. At the step 1060, scalar metric values determined at the step 1030, for example, M metric values corresponding to characteristic types 1 through M, are combined to form a single scalar metric value, T. In certain implementations, the value of T is determined by linearly weighing each of the determined M scalar metric values according to a prescribed cost function. The scalar value T therefore provides a measure of how closely a target optical sensor matches an optical front-end in terms of M characteristic values used to represent each of these devices. As an example, in certain implementations, a magnitude of each metric value represents a degree of difference between the candidate optical front-end and the target optical sensor (with larger magnitude values indicates a higher degree of difference) and the value of T is determined by summing the absolute value of each of the M scalar metric values. Thus, the value of T will be smaller as the candidate optical front-end matches the target optical sensor.

It will be understood that the process 1000 is illustrative and that modification and rearrangements may be made. For example, in certain implementations, some or all of the metrics determined at the step 1030 and/or the step 1060 may be non-scalar values. For example, one or more of these metrics may be represented as a vector, a matrix, as discrete and/or continuous functions of one or more parameters, and/or by any other suitable representation. Further, although the process 1000 illustrates comparing M characteristics of a target optical sensor with M characteristics of a candidate optical front-end on a pair-wise basis, other combination schemes may be used, including schemes that compare different numbers of characteristics from the target optical sensor and the candidate optical front-end to produce one or more metric values (for example, as a modification to the step 1030).

For illustrative purposes, portions of this disclosure have been described in the context of a PPG signal and a pulse oximetry monitor and system. However, it will be understood that the present disclosure is applicable to any suitable signal source that behaves as a low-noise optical current source for which a matched test signal is to be produced. For example, those skilled in the art will recognize that the present disclosure has wide applicability to other sensed signals including, but not limited to, other biosignals (for example, electrocardiogram, electroencephalogram, electrogastrogram, electromyogram, electrooculogram, heart rate signals, accelerometer signals, respiration monitor signals, pathological sounds, ultrasound, any other suitable biosignal) or combinations thereof. It will be understood that the methods disclosed herein may be implemented using any human-readable or machine-readable instructions on any suitable system or apparatus, such as those described herein.

It is to be understood that while various illustrative embodiments have been described, the forgoing description is merely illustrative and does not limit the scope of the invention. While several examples have been provided in the present disclosure, it should be understood that the disclosed systems, components, and methods may be embodied in many other specific forms without departing from the scope of the present disclosure.

The examples disclosed can be implemented in sub-combinations with one or more other features described herein. A variety of systems and methods may be implemented based on the disclosure and still fall within the scope of the invention. Also, the various features described or illustrated above may be combined or integrated in other systems or certain features may be omitted, or not implemented.

Examples of changes, substitutions, and alterations are ascertainable by one skilled in the art and could be made without departing from the scope of the information disclosed herein. Certain particular aspects, advantages, and modifications are within the scope of the following claims. All references cited herein are incorporated by reference in their entirety and made part of this application.

What is claimed is:

1. A current source for producing an output current that simulates a current generated by an optical patient sensor, the optical patient sensor including a sensor light source having a first characteristic profile and a sensor photodetector having a second characteristic profile, the current source comprising:

a light source configured to emit light in response to a drive signal, the light source having a characteristic profile that is similar to the first characteristic profile as to indicate interchangeability between the light source and the sensor light source;

a first photodetector configured to produce the output current in response to receiving light from the light source, the first photodetector having a characteristic profile similar to the second characteristic profile as to indicate interchangeability between the sensor photodetector and the first photodetector; and a control unit configured to:

receive a signal indicative of light emitted by the light source based on an output of a second photodetector;
provide the drive signal to the light source based at least in part on the received signal indicative of light emitted by the light source and a waveform control signal.

2. The current source of claim 1, wherein the first characteristic profile and the characteristic profile of the light source include at least one of a common manufacturing specification and a common manufacturing batch.

3. The current source of claim 2, wherein the first characteristic profile and the characteristic profile of the light source include a common manufacturing specification that includes at least one of an intensity, a propagation direction, a dispersion, a wavelength spectrum, a polarization, and a noise level.

4. The current source of claim 3, wherein the second characteristic profile and the characteristic profile of the first photodetector include at least one of a common manufacturing specification and a common manufacturing batch.

5. The current source of claim 4, wherein the second characteristic profile and the characteristic profile of the first photodetector include a common manufacturing specification that includes at least one of a noise level, a sensitivity, a spectral response, and a linearity.

6. The current source of claim 1, wherein the characteristic profile of the light source includes a characteristic with a value within a tolerance range of a value of a corresponding characteristic included in the first characteristic profile.

7. The current source of claim 6, wherein the characteristic profile of the first photodetector includes a characteristic with a value within a tolerance range of a value of a corresponding characteristic included in the second characteristic profile.

8. The current source of claim 1, further comprising a connector configured to couple the output current to a patient monitoring device.

9. The current source of claim 1, further comprising processing equipment configured to generate the waveform control signal based on at least one of a waveform stored in a memory and a user selection of one or more waveform features.

10. The current source of claim 9, wherein the processing equipment is included in a control module, and further comprising a connector configured to removably couple the current source to the control module.

11. The current source of claim 1, further comprising a temperature controller configured to hold relatively constant the temperature of at least one of the light source and the first photodetector.

12. The current source of claim 11, where the temperature of at least one of the light source and the first photodetector are held below an ambient temperature.

13. A method of manufacturing a current source for producing an output current that simulates a current generated by an optical patient sensor, the optical patient sensor including a sensor light source having a first characteristic profile and a sensor photodetector having a second characteristic profile, the method comprising:

selecting a light source having a characteristic profile similar to the first characteristic profile as to indicate interchangeability between the light source and the sensor light source;

selecting a photodetector having a characteristic profile similar to the second characteristic profile as to indicate interchangeability between the photodetector and the sensor photodetector, the photodetector configured to produce the output current in response to receiving light from the light source;

coupling the light source and photodetector to a control unit, the control unit, comprising a control photodiode, configured to provide a drive signal to the light source; and coupling a connector to the photodetector, whereby the output current is provided to the connector.

14. The method of claim 13, wherein selecting the light source comprises testing one or more characteristics included in the characteristic profile of the light source.

15. The method of claim 14, wherein selecting the photodetector comprises testing one or more characteristics included in the characteristic profile of the photodetector.

16. The method of claim 13, wherein the first characteristic profile and the characteristic profile of the light source include at least one of a common manufacturing specification and a common manufacturing batch.

17. The method of claim 16, wherein the at least one of a common manufacturing specification and a common manufacturing batch includes at least one of an intensity, a propagation direction, a dispersion, a wavelength spectrum, a polarization, and a noise level.

18. The method of claim 13, further comprising installing the current source within a test unit for a pulse oximetry monitor, wherein the connector is configured to couple with a pulse oximetry monitor connector to provide the output current to the pulse oximetry monitor.

19. The method of claim 18, wherein the connector is configured to couple with an optical patient sensor connector included with the pulse oximetry monitor.

20. The method of claim 13, further comprising coupling the control unit to a connector configured to removably couple the current source to a separate control module, the control module configured to provide a waveform control signal to the control unit and the control unit configured to provide a drive signal based at least in part on the waveform control signal.

21. The method of claim 20, further comprising providing a second current source for producing an output current that simulates a current generated by a second, different optical patient sensor, wherein the second current source is configured to couple to the control module after the current source is removed.

22. The method of claim 13, further comprising installing a light deflecting device to deflect at least some of the light emitted by the light source away from the photodetector.

* * * * *